United States Patent
Hung et al.

(10) Patent No.: US 9,144,414 B2
(45) Date of Patent: Sep. 29, 2015

(54) METHOD FOR QUANTIFYING DRUG DELIVERY USING CONTRAST-ENHANCED ULTRASOUND

(75) Inventors: Shuo-Hui Hung, Taipei (TW); Ran-Chou Chen, Taipei (TW); Tung-Hu Tsai, Taipei (TW)

(73) Assignee: Taipei City Hospital, Taipei (TW)

( * ) Notice: Subject to any disclaimer, the term of this patent is extended or adjusted under 35 U.S.C. 154(b) by 0 days.

(21) Appl. No.: 13/462,180

(22) Filed: May 2, 2012

(65) Prior Publication Data

US 2013/0116569 A1 May 9, 2013

(30) Foreign Application Priority Data

Nov. 3, 2011 (TW) .............................. 100140080 A

(51) Int. Cl.
*A61B 8/14* (2006.01)
*A61B 8/08* (2006.01)
*A61B 8/00* (2006.01)

(52) U.S. Cl.
CPC ............... *A61B 8/085* (2013.01); *A61B 8/0808* (2013.01); *A61B 8/4477* (2013.01); *A61B 8/481* (2013.01); *A61B 8/0891* (2013.01)

(58) Field of Classification Search
USPC ......................................... 600/458, 407, 437
See application file for complete search history.

(56) References Cited

U.S. PATENT DOCUMENTS

| | | | |
|---|---|---|---|
| 6,312,383 B1 * | 11/2001 | Lizzi et al. ..................... 600/437 |
| 2001/0021808 A1 * | 9/2001 | Shi et al. ......................... 600/438 |
| 2003/0220563 A1 * | 11/2003 | Schutt ............................ 600/431 |
| 2007/0207194 A1 * | 9/2007 | Grayburn et al. ............. 424/450 |
| 2008/0269668 A1 * | 10/2008 | Keenan et al. ................. 604/24 |
| 2008/0281205 A1 * | 11/2008 | Naghavi et al. ............... 600/458 |
| 2010/0158815 A1 | 6/2010 | Wang et al. |
| 2010/0196284 A1 | 8/2010 | Lindner et al. |
| 2011/0125080 A1 * | 5/2011 | Shi et al. ........................ 604/20 |

OTHER PUBLICATIONS

Ting, et al., "Concurrent blood-brain barrier opening and local drug delivery using drug-carrying microbubbles and focused ultrasound for brain glioma treatment", Biomaterials 33, 2012, pp. 704-712.
Eisenbrey, et al., "Development and optimization of a doxorubicin loaded poly (lactic acid) contrast agent for ultrasound directed drug delivery", Journal of Controlled Release 143, 2010, pp. 38-44.
Lampaskis, et al., "Investigation of the Relationship of Nonlinear Backscattered Ultrasound Intensity with Microbubble Concentration at Low MI", Ultrasound in Medicine and Biology, vol. 36, No. 2, 2010, pp. 306-312.

(Continued)

*Primary Examiner* — Joel F Brutus
(74) *Attorney, Agent, or Firm* — Muncy, Geissler, Olds & Lowe, P.C.

(57) ABSTRACT

The present invention relates to a method for quantifying drug delivery with the characteristic of measuring the signal intensity of peripheral vessels with a contrast-enhanced ultrasound to quantify the drug delivery at a target site. The present invention can be used for quantifying UTMD (ultrasound triggered microbubble destruction) targeted drug delivery, also for qualifying the unreleased amount of the long-acting drug in the tested object, and for helping setting the treatment schedule for ultrasound disruption of blood-brain barrier.

14 Claims, 8 Drawing Sheets

(56) References Cited

OTHER PUBLICATIONS

Tinkov, et al., "New doxorubicin-loaded phospholipid microbubbles for targeted tumor thereapy: In-vivo characterization", Journal of Controlled Release 148, 2010, pp. 368-372.

Hung, et al., "A Simple Method for Quantifying Ultrasound-Triggered Microbubble Destruction", Ultrasound in Medicine and Biology, vol. 37, No. 6, 2011, pp. 949-957.

Deckers, Roel et al., The Role of Ultrasound and Magnetic Resonance in Local Drug Delivery, J. Magn. Reson. Imaging, 2008, vol. 27, pp. 400-409.

* cited by examiner

METHOD FOR QUANTIFYING DRUG DELIVERY USING CONTRAST-ENHANCED ULTRASOUND

BACKGROUND OF THE INVENTION

1. Field of the Invention

The present invention relates to a method for quantifying drug delivery. More specifically, it relates to the method and the application for quantifying microbubble drug delivery using contrast-enhanced ultrasound.

2. Description of the Related Art

Ultrasound-Triggered Microbubble Destruction (UTMD) is a promising strategy to increase local drug concentration at pathologic site while reducing systemic toxicity wherein drug is loaded in micron-sized or nanometer-sized bubbles whose destruction is then triggered by ultrasound at the treatment site in order to deliver drug to the target. However, in clinical applications, other factors pose additional challenge. First, the ultrasound is attenuated to different degrees before they reach the target due to different tissue thickness and composition and tumor structure. Second, the concentration of micro-bubbles in the target area can vary depending on vascular factors such as tumor angiogenesis or tumor central necrosis. Third, if antibody-conjugated microbubbles are used, they will aggregate at specific sites so as to enhance the effect of ultrasound-triggered drug delivery. These factors will affect the actual amount of microbubble destroyed and influence the efficacy of drug delivery and a way to quantify ultrasound-triggered microbubble destruction will be useful to clinicians.

Several imaging modalities including magnetic resonance imaging (MRI), positron emission tomography (PET), single photon emission computed tomography (SPECT) and contrast-enhanced ultrasound (CEUS) have been used to monitor drug pharmacokinetics. However, all of these have their limitations. Despite the advantage of high tissue and spatial precision, none rigid pseudo signal and ionizing radiation of MRI, it doesn't allow to be used on individuals with implants such as pacemakers or defibrillators, the sensibility of partial contrast agent is inferior, and cannot provide fix-quantity drug delivery. On the other hand, the PET/SPECT requires radiolabelled microbubbles for depicting local drug concentration that risks the whole body of the subject under radiation.

Contrast-enhanced ultrasound imaging uses microbubbles loaded with filling gas. By means of the difference in echogenicity between the gas in the microbubbles and the soft tissue, it generates the reflected ultrasound and thus distinctive image with better contrast. While this method can assure the presence of microbubbles at the treatment site and is of the advantage of non-invasive, high resolution, instant scan, non-radioactive, low cost and user friendliness, the signal saturation of the image during the destruction of bubbles triggered by the ultrasound disqualifies the ultrasound as a quantifying tool. In recent studies, some scholars have attempted to quantify UTMD indirectly using a downstream method, by measuring the difference in echogenicity between and upstream location and a downstream location. However, in clinical operation, because the downstream vessel is a complex venous network that contains a mixture of sonicated and non-sonicated blood and the angiogenesis of tumors varies with different individuals. These make it difficult to measure vascular sonographic signal accurately, at or near the drug delivery zone.

SUMMARY OF THE INVENTION

The present invention provides an instant and quantificational UTMD drug delivery method and system.

Furthermore, this invention provides a method and system of measuring the released and unreleased amount of the fixed amount and long-lasting drug in the tested object with various time intervals and in a non-invasive way.

This invention also provides a schedule setting method and system for brain barrier treatment.

For achieving the above-mentioned purposes, the method for quantifying drug delivery at the target site in the present invention uses contrast agent to enhance the signal intensity while using ultrasound to assess the peripheral blood vessels. The method includes: a. an ultrasound device which produces a specific mechanical index of ultrasound; b. injecting a specific amount of ultrasound contrast agent into the tested object; c. measuring the ultrasound signal intensity of the peripheral blood vessels of the tested object with the contrast-enhanced ultrasound; d. calculating the real time systemic concentration of microbubbles based on the intensity variation of the ultrasound signal; and e. calculating the drug delivery at the target site based on the systemic concentration of microbubbles. Wherein the density of the microbubbles and the intensity of the ultrasound signal are of linear relation under the specific amount of ultrasound contrast agent.

In a preferred embodiment of the present invention, the ultrasound device is with a first ultrasound scanner to produce an ultrasound with low mechanical index whose energy level is not sufficient to trigger the microbubble destruction and to provide with the contrast-enhanced ultrasound image. The ultrasound device includes furthermore a second ultrasound scanner to produce an ultrasound with high mechanical index whose energy level is high enough to trigger the microbubble destruction at the target site for treatment. The first ultrasound device is used to record the ultrasound intensity at peripheral vessels and the second ultrasound device is used to trigger the microbubbles destruction at the target site and to obtain the attenuation amount and constant of the ultrasound signal. The systemic microbubble concentration can thus be calculated using the pharmacokinetic formula.

Furthermore, this invention includes: a quantifying system that monitors the drug delivery using the above-mentioned quantifying method, i.e., measuring the signal intensity of the peripheral vessels using a contrast-enhanced ultrasound system to quantify the drug delivery of a target site. The system includes: an injection device that injects microbubble contrast agent into the tested object via a catheter or an intravenous injection; an ultrasound device that records the variation of ultrasound signal intensity of the peripheral vessels of the tested object; and a signal processing device that processes the ultrasound signal data obtained from the peripheral vessels of the tested object, converts the data into systemic microbubble concentration and thus calculates the drug delivery at the target site.

Within certain microbubble concentration, the signal intensity of the ultrasound and the concentration of microbubbles are of direct proportion that is of the same characteristic as drug-loaded microbubbles. In addition, after ultrasound-triggered microbubble destruction, the concentration of microbubbles diminishes and the ultrasound signal weakens. Therefore, by using the method of the present invention, measuring the ultrasound signal intensity of peripheral vessels allows calculation of microbubble concentration of peripheral vessels that is the real time systemic microbubble concentration. By measuring the variation of systemic concentration of microbubbles, the pharmacokinetic of drug-loaded microbubbles can be understood.

Several aspects of the present invention will be illustrated in the following preferred embodiments and figures. Changes and modifications are possible within the spirit and scope of the novelty disclosed by the present invention.

For describing the main idea of the present invention as the summary mentioned above, the following preferred embodiments are illustrated in the attached figures. Similar elements are, to the extent possible, designated identical number in all the figures.

DETAILED DESCRIPTION

The characteristics and advantages of the present invention will furthermore be illustrated and explained in the following preferred embodiments. The preferred embodiments are for better illustration and not for limiting the scope of the present invention.

Following is the instruments, devices, methods and results in the preferred embodiments according to the present invention. The titles and subtitles in the preferred embodiments are set for facilitating the reader and not for limiting the scope of the present invention. Besides, some theories are suggested and disclosed in the present invention. While those theories can be true or false, all inventions applying those theories are within the scope of the present invention without considering any specific theory or application.

EMBODIMENTS

Embodiment 1

An Ultrasound Quantifying System for Monitoring Drug Delivery

Figure 1:
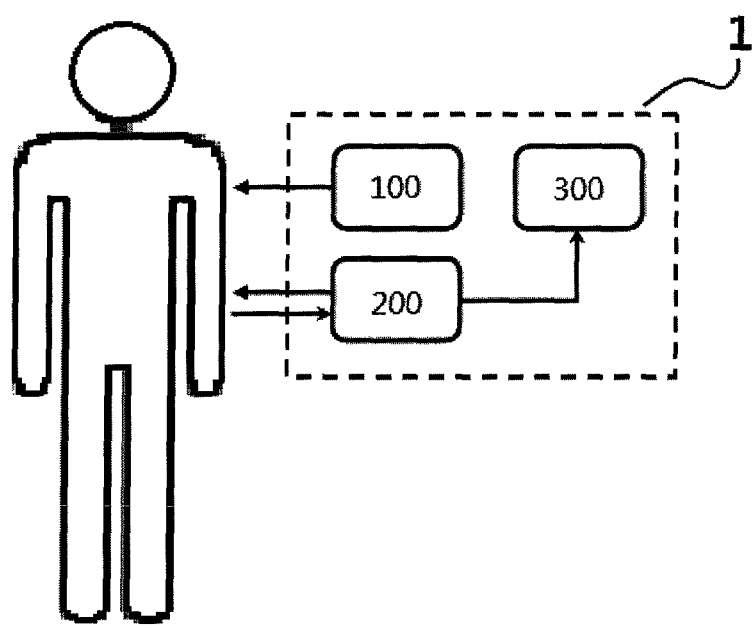
FIG. 1 is the basic structure of the ultrasound quantifying system for monitoring drug delivery.

The ultrasound quantifying system (1) for monitoring drug delivery uses a contrast-enhanced ultrasound system to measure the signal intensity of peripheral vessels in order to quantify the drug delivery at target site. FIG. 1 shows the basic structure of the ultrasound quantifying system (1) of the presentation. Wherein the ultrasound quantifying system (1) includes: an injection device (100) that injects microbubble contrast agent into the tested object via a catheter or an intravenous injection; an ultrasound device (200) that records the variation of ultrasound signal intensity of the peripheral vessels of the tested object; and a signal processing device (300) that processes the ultrasound signal data obtained from the peripheral vessels of the tested object, converts the data into systemic microbubble concentration and thus calculates the drug delivery at the target site.

Figure 3A:
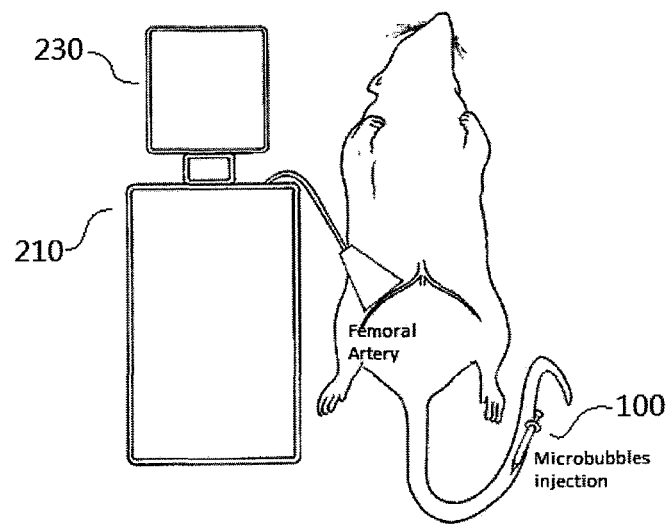
FIG. 3a/b is schematic diagram of the experimental setups of the ultrasound saturation experiment and the ultrasound triggered microbubble destruction experiment respectively.
Figure 3B:
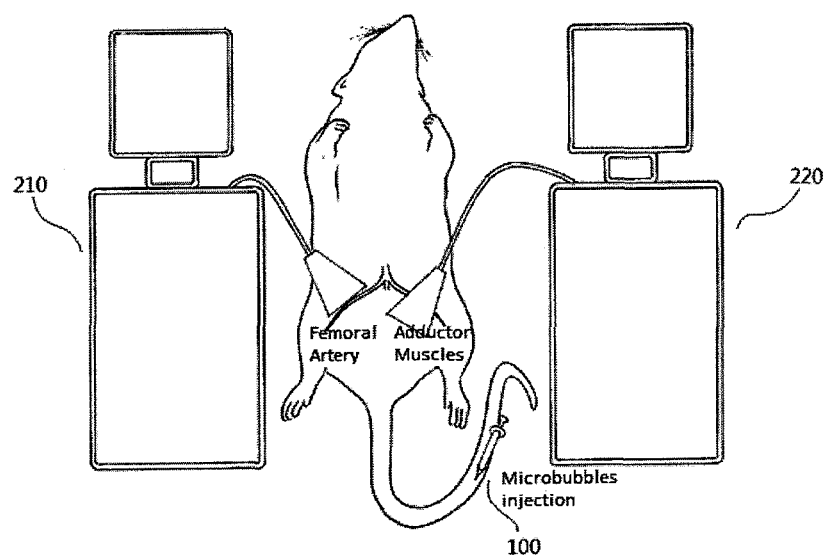

The ultrasound device (200) is with a first ultrasound scanner (210) to produce an ultrasound with low mechanical index to provide with the contrast-enhanced ultrasound image. Preferably, the ultrasound device (200) includes furthermore a second ultrasound scanner to produce an ultrasound with high mechanical index whose energy level is high enough to trigger the microbubble destruction as shown in FIGS. 3a and 3b. The first ultrasound device (210) produce an ultrasound with mechanical index (MI) <0.1 and the second ultrasound device (220) produce an ultrasound with mechanical index (MI) between 0.2~5.

Figure 2:
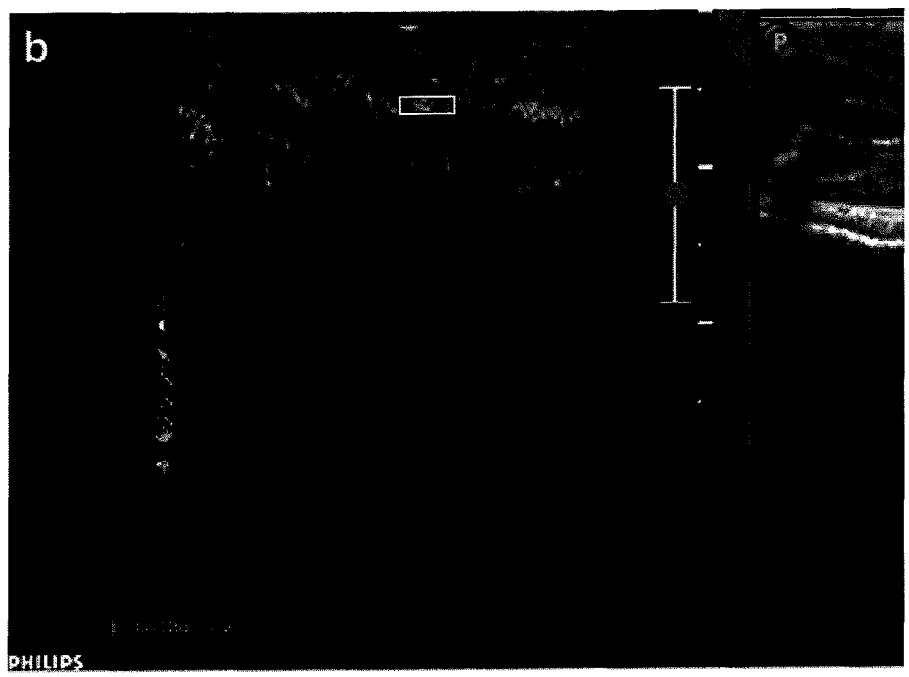
FIG. 2 is the ultrasound image of the region-of-interest (ROI).

The ultrasound device (200) can furthermore include a monitor (230). With the ultrasound image shown by the monitor (230), a region of interest (ROI) can be selected for signal analysis. In a preferred embodiment of the present invention, ROI=3×1 mm$^2$ as shown in FIG. 2.

The signal analysis software of the signal processing device (300) processes the ultrasound signal data and converts the data into a time-intensity curve (TIC) then gives quantitative result with the quantifying plug-in. Each experiment value is normalized with the baseline value (the average signal intensity before the injection of contrast agent). The standardized data is sent to the software MATLAB (The MathWorks, Natick, Mass., USA) to structure a non-linear curve using a ninth-order polynomial simulation. 3 parameters can be obtained using the TIC value: the peak signal intensity (PSI), the enhancement duration (ED) and the area under the signal intensity-time curve (AUC).

All the data obtained above are shown as "average±standard deviation" and statistically analyzed using the SPSS statistic software. The between group variance is tested using the analysis of variance (ANOVA). The TIC values of sham exposure and sonication under different MI are compared using ANOVA in order to analyze the relation between microbubble destruction and different MI. Each between-group variance is tested using pairing sample t and is statistically meaningful when $P<0.05$.

Embodiment 2

Ultrasound Signal Saturation Experiment

The rats averaging 330 g were anesthetized intraperitoneally with chloral hydrate of 450 mg/kg. Then the rats were placed in a supine position and the hairs of both things were shaved for ultrasound experiment. A 24-gauge catheter was placed in the tail vein and a three-way stopcock was attached to the end of the catheter with one branch used to administer microbubble contrast agents in the vein bolus and the second for flushing with physiologic saline. The microbubble contrast agents can be anyone of the following substances: ALBUNEX®, SONOZOID®, SONOVUE®, SONOVIST®, OPTISON®, LEVOVIST® or DEFINITY®. In this preferred embodiment, the powder contrast agent SonoVue (Bracco, Milan, Italy) was used in this study. 5 mL of physiologic saline was added to 25 mg of the powder in order to make a microbubble contrast agent suspension of sulfur hexafluoride with the average diameter of 2.5 μm which is considered to be of no difference with saline in terms of research security.

An ultrasound system (210) Philips iU22 was used for this study. It is equipped with a L12-5 linear array transducer (frequency range 5-12 MHz) for nonlinear harmonic imaging. A MI of 0.07 was used to avoid microbubble destruction. The right femoral artery is chosen for signal measurement. The probe of L12-5 array transducer was held orthogonal to the skin and parallel to the long axis of the thigh. Nonenhanced color-coded duplex ultrasound was used to identify the right femoral artery and then we immediately switched to contrast-enhanced mode for measurement of ultrasound signal. The experimental setup is shown in FIG. 3a.

SonoVue were administered to the rats via the vein bolus with different quantity (200, 400, 600 and 800 µg/kg). Sonographic recording of right femoral artery signal was started 15-30 seconds before each bolus injection of SonoVue and maintained for 6 minutes. In this time frame, 1980 images were acquired at a rate of 6 per second for signal analysis.

Figure 4:
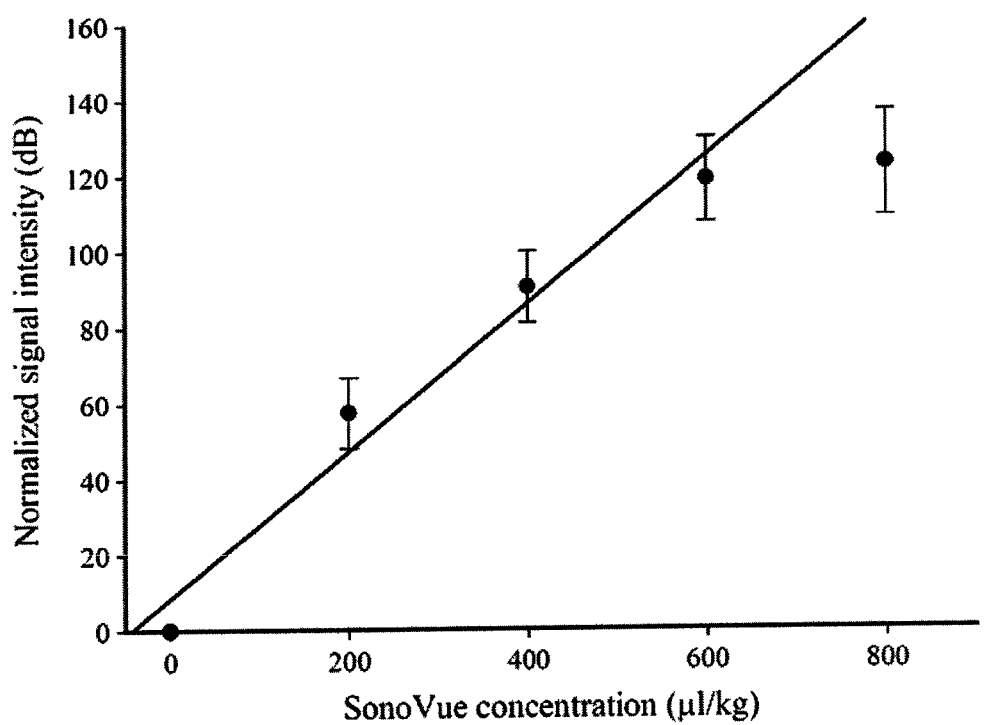
FIG. 4 is the relationship chart of the SonoVue concentration versus peak signal intensity (PSI) when using a L12-5 transducer to scan the right femoral artery of rat.

FIG. 4 shows the relationship between SonoVue concentration and peak signal intensity (PSI) when the right femoral artery was scanned with the L12-5 transducer, wherein the point zero of PSI represents the baseline signal intensity before SonoVue injection. The result shows that, when the SonoVue concentration is between 200-600 µL/kg, the microbubble concentration is proportional to the PSI value. The PSI data obtained within this concentration range and baseline were fitted with a straight line: y=0.195x+8.316 ($R^2$=0.911). The PSI did not differ significantly between SonoVue concentrations of 600 and 800 µL/kg, which suggest that ultrasound signal approaches the saturation under 600 µL/kg. It also shows that increasing SonoVue concentration beyond 600 µL/kg produces nonlinear concentration-intensity relationship that can lead to underestimation of systemic microbubble concentration. Therefore, the dose of 400 µL/kg was chosen for the subsequent investigations of microbubble destruction to insure the proportional relationship between the ultrasound signal and microbubble concentration.

Embodiment 3

Microbubble Destruction Experiment

In this preferred embodiment, two sets of ultrasound equipments are used. Besides the above-mentioned Philips iU22 ultrasound system (210), another Philips iU22 ultrasound system equipped with a L17-5 linear array transducer (220, frequency range 5~17 MHz) was used for microbubbles destruction. Wherein, for the first ultrasound system (210), the probe of L12-5 linear array transducer still held orthogonal to the skin and parallel to the long axis of the thigh and the right femoral artery is still chosen for signal measurement. And, for the second ultrasound system (220), the probe of L17-5 linear array transducer was held orthogonal to and in full contact with the skin of the left upper thigh and parallel to the long axis of the thigh. The ultrasound was focused on the adductor muscles of the left hind limb. The transducer position and contact area were the same for each experiment in this preferred embodiment. The experimental setup is shown in FIG. 3b.

Figure 5:
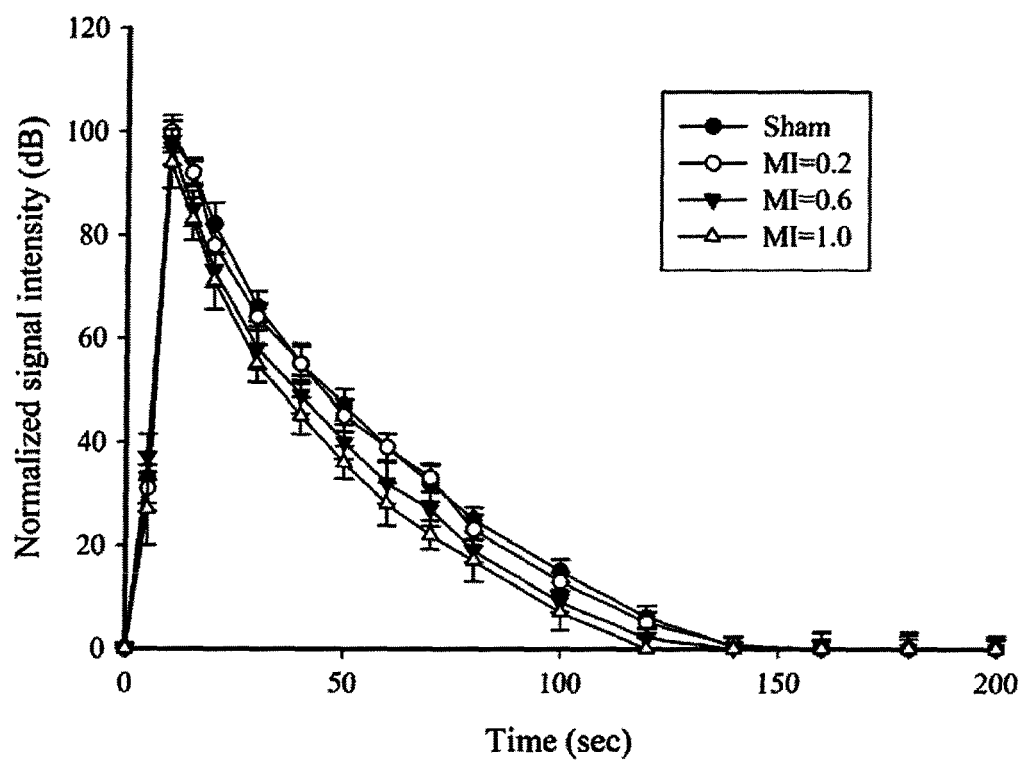
FIG. 5 is the time curve of the baseline-corrected femoral artery signal intensities for each imaging protocol: sham exposure, MI=0.2, MI=0.6 and MI=1.0.

Based on the result of signal saturation experiment of embodiment 2, we chose SonoVue of 400 µg/kg for microbubble destruction experiment. Eighteen rats were divided into three groups for experiment with one of the three MIs (0.2, 0.6 and 1.0). A sham exposure was performed first at the start of each group's experiment. Wherein, With the L17-5 transducer deactivated, the L12-5 transducer is used to capture signal as described in embodiment 2. The TIC of sham exposure ($TIC_0$) of right femoral artery bolus inject of SonoVue is obtained. This was followed by a 4-min time interval, after which the L17-5 transducer (positioned over the left thigh) was turned on for microbubble destruction and the TIC of the first sonication ($TIC_1$) is obtained. The above process was repeated again after a 4-min time interval to obtain the TIC of the second sonication ($TIC_2$). The results of shame exposure and microbubble destruction at different MIs (0.2, 0.5, 1.0) after baseline normalization are presented in FIG. 5.

Figure 6:
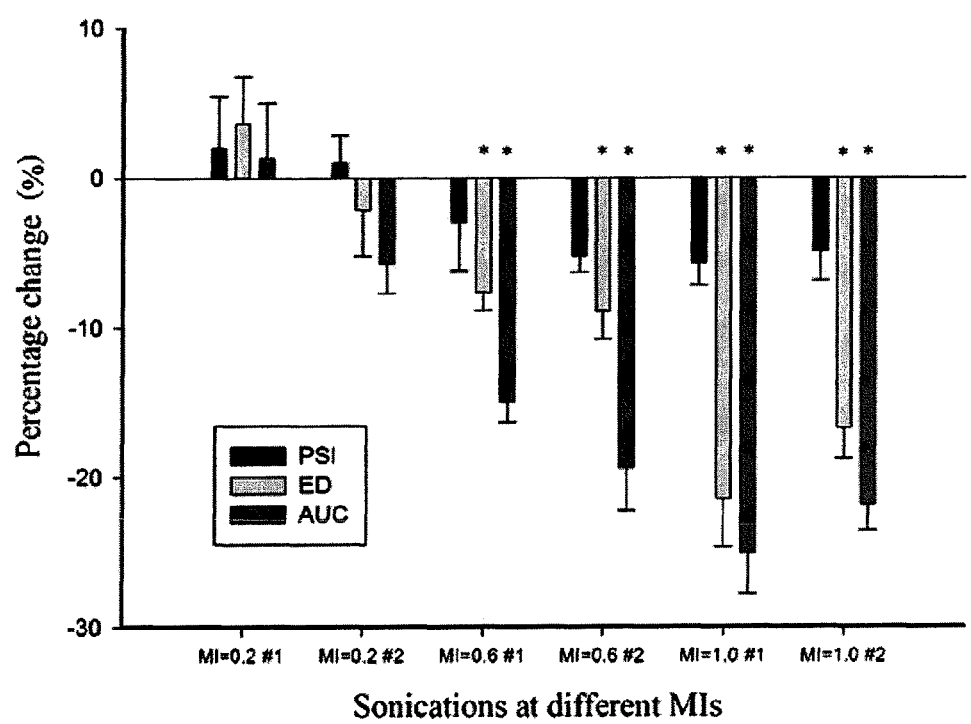
FIG. 6 compares the PSI, ED and AUC values of the first and second sonications at different MIs presented as percentage changes.

The $TIC_1$ and $TIC_2$ data was normalized to the $TIC_0$ data (e.g. $[TIC_1-TIC_0]/TIC_0$ and $[TIC_2-TIC_0]/TIC_0$, respectively) and this illustrates the efficacy of the first and second sonication. FIG. 6 shows different PSI, ED, AUC values of the first and second sonication in percentage. As a result, high MIs (0.6 and 1.0) decreased the AUC and ED but not the PSI. There were no significant differences in the PSI, ED and AUC between sonication at MI=0.2 and sham exposure or between MI=0.6 and MI=1.0. The PSI, ED and AUC did not differ significantly between the first and second sonication for each group. This shows that the microbubble concentration of the peripheral vessels that is estimated using the ultrasound image intensity of the peripheral vessels reflects the systemic concentration of microbubbles.

Embodiment 4

Pharmacokinetic Analysis

Compartmental models are classical Pharmacokinetic model to simulate the kinetic processes of drug absorption, distribution and elimination with little physiologic detail. In this embodiment, the one-compartment pharmacokinetic model is applied to estimate the UTMD at the target site. Pharmacokinetic calculations of the compartmental models were performed on each set of data of microbubble destruction using WinNonlin Standard Edition Vwesion 1.1 (Pharsight, Mountain View, Calif., USA) presented by the equation $C=Ae^{-\alpha t}$; where A is the intercept of the concentration for the slow disposition phase and $\alpha$ is the disposition rate constant. Data analysis after an intravenous injection at 2 mg/kg within 80 seconds yielded equations of $C=120.92e^{-0.01921t}$, $C=120.41e^{-0.0193t}$, $C=117.10e^{-0.0219t}$ and $C=115.87e^{-0.0243t}$ for sham exposure, MI=0.2, MI=0.6, and MI=1.0, respectively. Concerning Kinetics analysis data are listed shown in Table 1, the data is shown in "mean±standard deviation"; where AUC is the data of area under the time-intensity curve, $T_{1/2}$ is the elimination half-life, $C_{max}$ is the maximum intensity, CL is the clearance, MRT is the mean residence time and $V_{ss}$ is the distribution at steady-state.

TABLE 1

| Pharmacokinetics Analysis | | | | |
|---|---|---|---|---|
| | Sham | MI 0.2 | MI 0.6 | MI 1.0 |
| AUC (dBs) | 6262.0 ± 86.9 | 6218.3 ± 102.0 | 5320.3 ± 66.0 | 4745.9 ± 69.2 |
| $T_{1/2}$ (s) | 36.1 ± 0.8 | 36.0 ± 0.4 | 31.4 ± 0.8 | 28.3 ± 0.7 |
| $C_{max}$ (db) | 120.4 ± 2.3 | 119.8 ± 1.7 | 117.6 ± 2.5 | 116.7 ± 3.2 |

TABLE 1-continued

Pharmacokinetics Analysis

|  | Sham | MI 0.2 | MI 0.6 | MI 1.0 |
|---|---|---|---|---|
| CL (µL/s) | 0.3 ± 0.0 | 0.3 ± 0.0 | 0.4 ± 0.0 | 0.4 ± 0.0 |
| MRT (s) | 52.1 ± 1.1 | 52.0 ± 0.6 | 45.3 ± 1.1 | 48.0 ± 1.0 |
| $V_{ss}$ (µL) | 16.7 ± 0.3 | 16.7 ± 0.2 | 17.0 ± 0.4 | 17.2 ± 0.5 |

Embodiment 5

Monitoring Unreleased Quantity of Long-Acting Drug in the Tested Object

As shown in the previous embodiments, by measuring the ultrasound signal intensity of peripheral vessels, we can estimate real time systemic microbubble concentration. And the pharmacokinetics models allow the estimation of the UTMD amount or the amount of metabolism of microbubbles in vivo during a period of time. Therefore, another application of the present invention is further elaborated in this embodiment: quantifying the released and unreleased amount of long-acting drug in the tested object as shown in FIG. 7.

Figure 7:
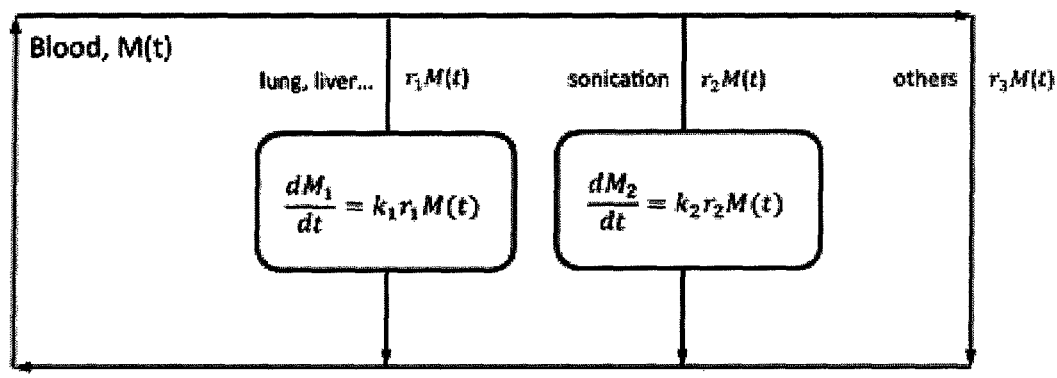
FIG. 7 is the schematic representation of the drug-loaded microbubbles circulation in vivo.

FIG. 7 is the schematic diagram of the in-body circulation of drug-loaded microbubbles. Where M(t) is the concentration of drug-loaded microbubbles in the blood, $M_1$ is the concentration of drug-loaded microbubbles in the organ, $M_2$ is the concentration of drug-loaded microbubbles triggered under sonication; $r_1$ is the bloodstream index in main metabolic organs, $r_2$ is the bloodstream index in the sonication site and $r_3$ is the residue; and K1 is the decay coefficient in the organ, k2 is the decay coefficient in the sonication site. Based on mass balance, the variation of drug-loaded microbubbles in the blood is the sum of the variation in the organs and ultrasound triggered one. Thus, we get the following equation:

$$\frac{dM}{dt} = -\frac{dM_1}{dt} - \frac{dM_2}{dt}$$
$$= -k_1 r_1 M(t) - k_2 r_2 M(t)$$
$$= (-k_1 r_1 - k_2 r_2) M(t)$$

Using Laplace transform, the following equations can be used to obtain the concentration of the drug-loaded microbubbles triggered under sonication.

$$M(t) = M_0 \exp(-k_1 r_1 - k_2 r_2)t$$

$$dM(t) = (-k_1 r_1 - k_2 r_2) M(t) dt$$

In the case where the microbubbles are loaded with long-acting drugs, body tissues, such as liver, will not destroy the microbubbles. We can thus assume the value of $k_1 r_1$ is close to zero. Therefore, the concentration of microbubbles in the blood measured can be used to estimate the concentration of UTMD. From this, the quantifying method of the present invention allows quantification of the real time concentration of the drug-loaded microbubbles in the tested object with various time intervals and in a non-invasive way, as well as measurement of the released and unreleased amount of the long-acting drug in the tested.

Embodiment 6

Blood-Brain Barrier Experiment

Figure 8:
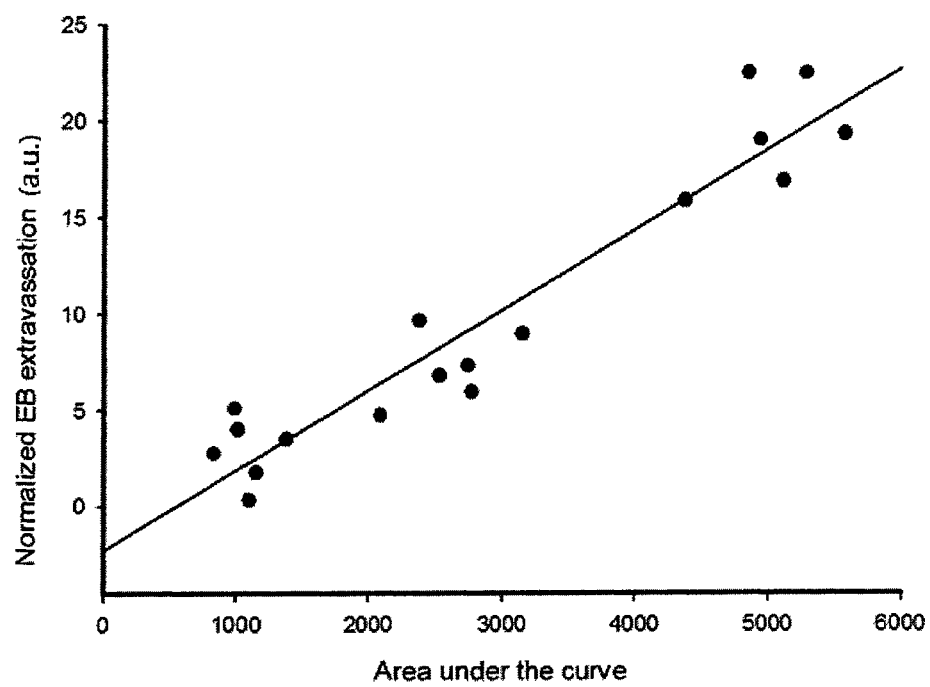
FIG. 8 is relationship chart of the AUC (area under the signal-intensity vs. time curve) and Evans Blue extravassation while injecting different doses of microbubbles.

Previous studies showed that that the ultrasound (or focused ultrasound) while merged with microbubbles creates void effect that can be used to the reversible disrupt of the blood-brain barrier and to increase the permeability of the membrane and the cell gap. The same principle can be applied to the local drug delivery in the brain. There are also studies that showed that increasing the amount of microbubbles could increase the drug delivery. FIG. 8 is the diagram of the relationship between AUC (the area under the time-signal curve) and Evans Blue extravasation. It shows that the AUC measured using the quantifying method of the present invention is proportional to the drug delivery. It also shows that the quantifying method using contrast-enhanced ultrasound to monitor the signal intensity of peripheral vessels in order to estimate real time concentration of systemic microbubble can help to set the treatment schedule for ultrasound blood-brain barrier disruption.

While the invention has been described in connection with certain embodiments, it is not intended to limit the scope of the invention to the particular forms set forth, but, on the contrary, it is intended to cover such alternatives, modifications, and equivalents as may be included within the spirit and scope of the invention.

There have been described and illustrated herein several embodiments in order to better illustrate the principle and application of the present invention and to allow those who are equipped with common knowledge in the technical field to utilize this invention and its embodiments and to modify for meeting specific need. While particular embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

The characteristics disclosed in the present invention can be combined in any combination. Each characteristic disclosed in the present invention can be replaced by same, equivalent or similar characteristics. Therefore, unless specified otherwise, each characteristic disclosed is merely an embodiment of a series of equivalent objects or similar characteristics.

Based on the prior description, people familiar with the art can easily identify the basic characteristics of the present invention. Various modifications may be made to this invention for different usages and situations without departing from the scope covered by the appended claims. Any modification or change not departing from the main idea of the present invention is within the scope of the patent claimed.

What is claimed is:

1. A method for quantifying drug delivery with a characteristic of measuring a variation of a signal intensity of peripheral vessels using contrast-enhanced ultrasound, comprising:
   a. producing an ultrasound with a specific mechanical index (MI) by an ultrasound device;

b. injecting a specific dose of ultrasound contrast agent into a tested object;

c. triggering microbubbles destruction at the target site of the tested object by a ultrasound of high mechanical index;

d. monitoring an ultrasound signal intensity of the peripheral vessels in a remote region from the target site using a contrast-enhanced ultrasound of low mechanical index;

e. determining, by a processor, an attenuation amount A and an attenuation constant $\alpha$ of the ultrasound signal monitored in the step d based on the microbubble destruction triggered by the sonication in the step c;

f. calculating, by the processor, a real time systemic microbubble concentration by using a pharmacokinetic formula $C=Ae^{-\alpha t}$; and g. quantifying, by the processor, the drug delivery at a target site based on the real time systemic microbubble concentration.

2. The method as in claim 1, wherein the drug delivery is loaded by microbubbles.

3. The method as in claim 1, wherein the specific dose of ultrasound contrast agent is in the range where the systemic microbubble concentration is proportional to the ultrasound signal intensity.

4. The method as in claim 1, wherein the ultrasound device produces the ultrasound of low mechanical index whose energy is not sufficient to trigger the microbubble destruction in order to obtain a contrast-enhanced ultrasound image.

5. The method as in claim 4, wherein the low mechanical index (MI) of ultrasound <0.1.

6. The method as in claim 1, wherein the ultrasound devices includes:
a first ultrasound scanner to produce the ultrasound of low mechanical index; and
a second ultrasound scanner to produce the ultrasound of high mechanical index.

7. The method as in claim 6, wherein the ultrasound of low mechanical index produced by the first ultrasound scanner is of energy that is not sufficient to trigger the microbubble destruction in order to obtain a contrast-enhanced ultrasound image for recording the ultrasound signal intensity at peripheral vessels.

8. The method as in claim 6, wherein the ultrasound of high mechanical index produced by the second ultrasound scanner is of energy that is sufficient to trigger the microbubble destruction at the target site.

9. The method as in claim 6, wherein the low mechanical index (MI) of the ultrasound produced by a first sonication <0.1 and the high mechanical index (MI) of the ultrasound produced by a second sonication is between 0.2-5.

10. The method as in claim 1, wherein the method is used to quantify an unreleased amount of a long-acting drug in the tested object.

11. The method as in claim 1, wherein the method is used to monitor the real time systemic microbubble concentration to ensure an occurrence of void effect in order to assist to set an ultrasound disruption of blood-brain barrier treatment schedule.

12. A quantifying system to monitor drug delivery that measures a variation of a signal intensity of peripheral vessels with a contrast enhanced ultrasound system in order to quantify a drug delivery at a target site, wherein the quantifying system includes:
an injection device that injects microbubble contrast agent into the tested object via a catheter or an intravenous injection;
a first ultrasound device produces a ultrasound of high mechanical index that triggers microbubbles destruction at the target site of a tested object;
a second ultrasound device produces a ultrasound of low mechanical index that records a variation of ultrasound signal intensity at the peripheral vessels in a remote region from the target site; and
a signal-processing device that determines am attenuation amount A and an attenuation constant $\alpha$ of ultrasound signal based on a microbubble destruction red b a sonication, processes an ultrasound signal data obtained from the peripheral vessels of the tested object, converts the ultrasound signal data into systemic microbubble concentration by using a pharmacokinetic formula $C=Ae^{-\alpha t}$, and thus quantifies calculates the drug delivery at the target site based on the systemic microbubble, concentration.

13. A quantifying system as in claim 12, wherein an ultrasound produced by the first ultrasound device is of mechanical index <0.1.

14. A quantifying system as in claim 12, wherein the ultrasound produced by the second ultrasound scanner is of mechanical index between 0.2-5.

* * * * *